United States Patent [19]

Gressel et al.

[11] Patent Number: 5,209,927

[45] Date of Patent: * May 11, 1993

[54] OPHTHALMIC SOLUTION

[75] Inventors: Philip D. Gressel, Everman; Robert E. Roehrs; Robert G. Harris, both of Fort Worth, all of Tex.

[73] Assignee: Alcon Laboratories, Inc., Ft. Worth, Tex.

[ * ] Notice: The portion of the term of this patent subsequent to Dec. 24, 2008 has been disclaimed.

[21] Appl. No.: 716,426

[22] Filed: Jun. 17, 1991

Related U.S. Application Data

[63] Continuation of Ser. No. 331,478, Mar. 31, 1989, abandoned, which is a continuation of Ser. No. 908,469, Dec. 5, 1986, abandoned, which is a continuation of Ser. No. 700,861, Jan. 23, 1985, abandoned.

[51] Int. Cl.$^5$ ............................................. A61K 31/74
[52] U.S. Cl. .................................... 424/78.04; 514/915
[58] Field of Search ................. 424/78, 81, 915, 78.04

[56] References Cited

U.S. PATENT DOCUMENTS

| | | | |
|---|---|---|---|
| 3,843,782 | 10/1974 | Krezanoski et al. | 424/677 |
| 3,920,810 | 11/1975 | Rankin | 424/78.04 |
| 3,987,163 | 10/1975 | Rankin | 424/78.04 |
| 4,003,991 | 1/1977 | Krohn et al. | 424/81 |
| 4,008,321 | 2/1977 | Kamishita et al. | 424/243 |
| 4,039,662 | 8/1977 | Hecht et al. | 514/59 |
| 4,131,651 | 12/1978 | Shah et al. | 424/78.04 |
| 4,271,143 | 6/1981 | Schoenwald et al. | 424/78 |
| 4,343,787 | 8/1982 | Katz | 424/78 |
| 4,407,792 | 10/1983 | Schoenwald et al. | 424/81 |
| 4,521,414 | 6/1985 | Chiou et al. | 514/229 |

FOREIGN PATENT DOCUMENTS 2007091A 5/1979 United Kingdom .

OTHER PUBLICATIONS

Handbook of Non Prescription Drugs, fifth edition, pp. 229-235.
Chemical Abstracts, 93:120423g (1980).
Chemical Abstracts, 92:220622u (1980).
Chemical Abstracts, 98:95611k (1983).

Primary Examiner—Frederick E. Waddell
Assistant Examiner—Zohreh A. Fay
Attorney, Agent, or Firm—Gregg C. Brown; James A. Arno; Julie J. L. Cheng

[57] ABSTRACT

Disclosed is a liquid ophthalmic composition of unique rheological and lubricating properties comprising, inter alia, a polyanionic polymer for use as a long lasting artificial tear. Also disclosed is a method of treatment comprising topically administering the composition when indicated for relief of dry eye syndrome, foreign body sensation, burning, hyperemia, corneal staining, and the like.

10 Claims, No Drawings

OPHTHALMIC SOLUTION

This is a continuation of U.S. patent application Ser. No. 07/331,478, filed Mar. 31, 1989 now abandoned, which is a continuation of Ser. No. 06/908,469, filed Dec. 5, 1986 now abandoned, which is a continuation of Ser. No. 06/700,861, filed Jan. 23, 1985, now abandoned.

BACKGROUND OF THE INVENTION

The present invention relates to liquid ophthalmic compositions for human and veterinary use comprising, inter alia, in an aqueous vehicle, a class of polyanionic polymers which, because of their unique combination of mucomimetic, rheological, and lubricating properties, are useful as long lasting, topically applied agents for relief of dry eye syndrome, foreign body sensation, burning, hyperemia, corneal staining, and the like. The ophthalmic compositions are also useful as lubricating and cushioning agents for the eye after traumatic injury or surgery. They may also be used as corneal wetting and lubricating agents for use with contact lenses, and in various eye irritation disorders.

The present invention also relates to a method of treating eyes by topically applying the ophthalmic solutions of the present invention when indicated for the relief of dry eye syndrome and when indicated to achieve the other effects mentioned above. Dry eye syndrome, and related eye ailments, including mere transitory discomforts, are well known in the scientific and patent literature. The following patents are incorporated herein by reference to the extent that they provide additional background on the syndrome and recognized indications for its relief: U.S. Pat. Nos. 4,039,662; 3,987,163; 3,920,810; 3,843,782; and 4,131,651; and Belgian Patent 844,544.

However, none of these prior art formulations meet all of the important criteria for an effective and long lasting treatment of dry eye syndrome, particularly the moderate to severe Kerato-conjunctivitis sicca (KCS) patient. These prior art attempts fall into three categories corresponding to their physical state: liquids, anhydrous ointments, and solids. The solids are in the form of ocular inserts which slowly dissolve or erode to provide a thickened tear film. While these have the potential for providing longer term symptomatic relief than liquids, few patients are willing to persist in using them since they are difficult to insert and, once in place, tend to be uncomfortable, frequently themselves causing the foreign body sensation they were meant to treat. Prior liquid and ointment formulations, while giving the sensation of relief, are strictly palliatives without long-term effect.

Thus, the search for an easy to use (especially by infirmed patients via self-medication), long lasting (4 to 24 hours) ophthalmic preparation for treating the effects described collectively under the dry eye syndrome and having the ancillary utilities mentioned above continues.

DETAILED DESCRIPTION OF THE INVENTION

The ophthalmic formulations of the present invention are viscous aqueous solutions which are capable of being administered as liquid drops, and which comprise, in addition to conventional ingredients imparting, for example, bacteriostatic and formulatory balance functions, a critical polyanionic polymer.

POLYANIONIC POLYMER COMPONENT

The high molecular weights polymers useful in the present invention have a molecular weight of from about 400,000 to about 6 million. The polymers are characterized as having carboxylic functional groups and preferably contain from 2 to 7 carbon atoms per functional group. The viscous solutions which form during the preparation of the ophthalmic polymer dispersion have a viscosity of from about 10 to about 20,000 cps (spindle 7 at 20 RPM) at 25° C. generated by an RVT Brookfield Viscometer, preferably from about 5,000 to about 20,000 cps. The solutions further are characterized as having a yield value of from about 50 to about 1,500 dyne/cm$^2$ as determined by a Ferranti-Shirley Viscometer at 25° C.

The high molecular weight polymers used in the compositions of the present invention not only thicken the compositions to provide a semi-viscous state, but they also provide a special type of rheology, i.e., plastic viscosity.

Plastic viscosity is indicative of a material that does not flow until a certain force or stress value is exceeded. This is referred to as the yield value. While not wishing to be bound by any theory, it is believed that the increased duration of activity of the gel compositions of the invention is related not only to the apparent viscosity (thickness), but is also related to the yield value. The gel compositions of the present invention exhibit unique response to shear stress. When the yield value is exceeded, the gel structure is altered temporarily, allowing the gel to flow under stress. In the eye, this corresponds to the blinking eyelid. When the stress is removed (eyelid at rest) the structure of the gel is partially re-established.

The high molecular weight polymers useful in the ophthalmic compositions of the present invention provide unique rheological characteristics, combining high viscosity with yield values at the levels set forth herein above. They confer lubricative properties, and are polyanionic in charge character owing to their carboxylic acid functional groups. While the claimed invention will not be limited by any theory of action, but in the sense of providing a functional definition, it will be noted that these polyanionic charged polymers appear to function by maintaining or restoring the normal hydration equilibrium of the epithellial cells, protecting the cornea in a manner similar to that believed to be provided by the mucin component of normal tears. Therefore, in theory, the polymers, in addition to being well retained in the eye and providing lubrication, can function as a mucin substitute in the dry eye syndrome where there is a deficiency or absence of the natural mucin component of the normal tears.

Suitable polymers useful in the present invention are carboxyl vinyl polymers. Preferred polymers of this class include Carbomers, available under the trade name Carbopol from the B. F. Goodrich Company. The known and readily available polymers Carbopol 934 and 940 are specifically preferred. The polymers are used in the instant aqueous compositions at a level of from about 0.05 to about 0.25 percent by weight.

STABILIZING AGENT

A stabilizing agent may be required to maintain the hydration state of the polymer during long storage.

While not imposing any limitation by theory of action, but in the interest of describing function, it should be noted that associations appear to occur within or among the polymer chains which, after time, favor the reduction of hydration state of the polymer chains. These may be in the form of hydrogen bonds within and among the polymer chains. This can manifest itself as a change in viscosity and texture of the ophthalmic solutions of the present invention. Agents which greatly decelerate or eliminate this aging process in the instant compositions are generically polyols at a concentration range of from 0.2% to 5% by weight. Representative of such polyols are mannitol, sorbitol, glycerol, sucrose, related sugars, and the like, in the above-recited concentration range. An especially preferred stabilizing agent is mannitol at a concentration of from 0.2% to 5% by weight.

OTHER INGREDIENTS

Antimicrobial Preservative

Ophthalmic products are package in multiple use containers as a general rule. Preservatives may be incorporated to prevent contamination of the products when they are exposed to microorganisms during use. One or more preservatives and ancillary agents may be chosen from, for example: benzalkonium chloride, thimerosal, chlorobutanol, methyl paraben, propyl paraben, phenylethyl alcohol, edetate disodium, sorbic acid, Onamer M (Onamer M is available from Onyx Chemical Company, Jersey City, N.J.), or other agents known to those skilled in the art. Typically such preservatives are employed at a level of from 0.001% to 1.0% by weight. If no preservative is desired, the gels may be sterile packaged in unit-of-use containers. With respect to the use of Onamer M, co-pending, commonly assigned U.S. patent application Ser. No. 306,317 filed 9/28/81 is incorporated herein by reference to the extent that it describes Onamer M.

Neutralizing Agents

The polyanionic polymers may be neutralized to the desired pH with basic chemicals such as sodium hydroxide, ammonium hydroxide, ethanolamine, urea, and selected amines. Mineral acids such as hydrochloric, phosphoric or sulfuric may be used to adjust pH toward acidity. The preferred pH range is from 4.5 to 8.5.

Tonicity Agents

The tonicity of the gels can be adjusted to either hypotonicity, isotonicity or hypertonicity relative to normal tears by use of generally used materials known to the art. Sodium chloride is a preferred tonicity agent. The stabilizing agents confer a proportion of the desired tonicity, or may provide sufficient tonicity so that no additional agents are required.

FORMULATION

The following compounding procedure may be used for sterile manufacturing. A dispersion of polymer is made in either purified water or a dilute acid solution. All other components are dissolved in purified water and added to the polymer dispersion. The dispersion is sterilized by autoclaving or by heating in a pressurized vessel to sterilizing temperature 121° C, for thirty minutes. The base is added aseptically by methods generally known to the art. The pH is measured and adjusted aseptically and the final weight is adjusted with sterilized purified water. Specific examples are detailed below.

PHYSICAL PROPERTIES

The viscosity, Brookfield RVT, measured at ambient room temperature, may be between 10 centipoises and 20,000 centipoises using spindle 7. Preferably the viscosity is between 5,000 and 15,000 centipoises using spindle 7 at 20 RPM. Viscosity measurements are made after entrapped air is removed. The pH is between 4.5 and 8.5; the especially preferred range in 5.5. to 8.0. The final ophthalmic solution is clear or nearly clear, smooth, homogeneous, and pourable.

USE

The artificial tear solutions represented by the present invention are intended for relief of dry eye syndromes, particularly kerato-conjunctivitis sicca. These symptoms include, inter alia, foreign body sensation, burning, and hyperemia. Additionally, the instant ophthalmic solutions can halt the progress of the syndrome and reverse its effects including, in moderate to severe cases of dry eye, corneal staining, which is made evident by use of Rose Bengal or Fluorescein. The dosage regimen is typically one or two drops dispensed from a standard ophthalmic dropping device, such as, glass or plastic dropping pipets or plastic bottles fitted with a dropper orifice. Individual drops are within the range of 5 to 75 mg. The drops are placed onto the corneal or scleral surface, or into the lower conjunctival sac. Frequency of dosing is variably dependent upon the severity of the syndrome. For severe cases dosing may occur four or more times per day. The frequency is reduced when signs of the disease state show improvement. At that time dosing may be as infrequent as one dose daily or once every two or three days.

The following Examples are intended to further illustrate, but not to limit, the compositions of the present invention.

EXAMPLE 1

|  | % by weight | Amounts |
| --- | --- | --- |
| Carbopol 940 | 0.2 | 320 grams of slurry A |
| Hydrochloroic Acid | q.s. | (5% Carbopol & 1.9% in HCl) |
| Mannitol | 3 | 1600 ml of solution B |
| Edetate Disodium | 0.01 |  |
| Benzalkonium Chloride (plus 10% compounding excess) | 0.008 | 7.04 ml of Solution C |
| Sodium Hydroxide | q.s. pH 7 | 25 ml of 6N |
| Purified Water | q.s. ad 100 | q.s. ad 8000 grams |

A slurry is made in which 5% Carbopol is sifted into a dilute acid solution (1.9% of 1N HCl) using a propeller mixer to form a vortex. The slurry (A) is mixed until it is free from visible lumps. It is then filtered by pumping through a cartridge filter to remove small particles. Then it is autoclaved for 30 minutes at 121° C. and subsequently handled aseptically using methods known to the art. A stock solution (B) of 0.05% edetate disodium and 15% mannitol in purified water is prepared by heating to 60° C. and sterile filtering through a 0.22 micron membrane filter maintained at a warm temperature. The sterile-filtered solution is also maintained warm until its use. A stock solution (C) of benzalkonium chloride 10% in purified water is sterile filtered and handled aseptically.

The gel is compounded on a laminar-flow bench using aseptic technique. The slurry (A) is weighted into a tared mixing bowl. Solution C is added slowly with mixing. When it is well dispersed, solution B is incorporated and mixed well until the slurry is once again homogeneous. The pH is adjusted with 6N sodium hydroxide with constant mixing while the base is added. The final weight is adjusted to 8000 grams with sterile purified water. The gel is once again mixed until it is homogeneous.

The Brookfield viscosity is obtained by centrifuging a sample of the gel to remove visible air bubbles. Spindle 7 is inserted carefully into the centrifuge tube and positioned appropriately. The 20 RPM setting is used. Viscosity measurements are 12,400 centipoises and 12,600 centipoises. The pH is 7.17. The appearance is that of a smooth, clear, pourable gel.

EXAMPLE 2

|  | % by weight | Amounts |
| --- | --- | --- |
| Carbopol 940 | 0.2 | 20 g of slurry of |
| Hydrochloric Acid, 1N | q.s. | 5% Carbopol & 1.9% 1N HCl |
| Edetate Disodium | 0.01 | 50 ml of 10X solution |
| Onamer M | 0.001 | 1.0 ml of 0.5% solution |
| Sodium Hydroxide, 6N | q.s. ad pH 7 | 1.7 ml |
| Purified Water | q.s ad 100 | q.s. ad 500 g |

The procedure is as described in Example 1. Viscosity measurements are 14,200 and 15,200 centipoises. Appearance is that of a smooth, clear, pourable gel.

EXAMPLE 3

|  | % by weight | Amounts |
| --- | --- | --- |
| Carbopol 940 | 0.1 | 10 g of slurry of |
| Hydrochloric Acid, 1N | q.s. | 5% Carbopol and 1.9% 1N HCl |
| Edetate Disodium | 0.01 | 50 ml of 10X solution |
| Benzalkonium Chloride (plus 10% compounding excess) | 0.008 | 4.4 mls of 1% solution |
| Sodium Hydroxide, 6N | q.s. ad pH 7 | About 1 ml: q.s. ad pH 7 |
| Purified Water | q.s. ad 100 | q.s. ad 500 | the procedure is as described in Example 1. Viscosity is 1,200 centipoises. Appearance is that of a smooth, clear, pourable gel.

EXAMPLE 4

|  | % by weight | Amounts |
| --- | --- | --- |
| Carbopol 934 | 0.2 | 320 grams of slurry A |
| Hydrochloric Acid | q.s. | (5% Carbopol and 1.9% 1N HCl) |
| Mannitol | 3 | 1600 ml of solution B |
| Edetate Disodium | 0.01 |  |
| Benzalkonium Chloride (plus 10% compounding excess) | 0.008 | 7.04 mls of solution C |
| Sodium Hydroxide | q.s. pH 7 | Approx. 25 ml of 6N |
| Purified Water | q.s. ad 100 | q.s. ad 800 grams |

Procedure is as described in Example 1.

What is claimed is:

1. A method of treating dry eye syndrome in mammalian hosts which comprises applying topically to the affected eye a therapeutically effective amount of a sterile, aqueous ophthalmic solution, said ophthalmic solution consisting essentially of 0.05% to 0.25% by weight of a carboxy vinyl polymer having a molecular weight in the range of 400,000 to 6,000,000, and water, said solution having a yield value in the range of 50 to 1,500 dyne/cm$^2$.

2. The method of claim 1, wherein one to two drops of the ophthalmic solution are applied to the affected eye.

3. The method of claim 1, wherein the ophthalmic solution has a viscosity in the range of 10 to 20,000 centipoise.

4. The method of claim 1, wherein the ophthalmic solution has a viscosity in the range of 5,000 to 15,000 centipoise.

5. The method of claim 1, wherein the ophthalmic solution has a pH in the range of 4.5 to 8.5.

6. The method of claim 1, wherein the concentration of the carboxy vinyl polymer is in the range of 0.1% to 0.2% by weight.

7. An aqueous ophthalmic solution for the treatment of dry eye syndrome, consisting essentially of 0.05% to 0.25% by weight of a carboxy vinyl polymer having a molecular weight in the range of 400,000 to 6,000,000, and water, said solution having a yield value in the range of 50 to 1,500 dyne/cm$^2$.

8. The ophthalmic solution of claim 7, wherein the ophthalmic solution has a viscosity in the range of 10 to 20,000 centipoise.

9. The ophthalmic solution of claim 7, wherein the viscosity of the solution is in the range of 5,000 to 15,000 centipoise.

10. The ophthalmic solution of claim 7, wherein the pH of the solution is in the range of 4.5 to 8.5.

* * * * *